(12) United States Patent
Zhang et al.

(10) Patent No.: US 7,157,237 B2
(45) Date of Patent: Jan. 2, 2007

(54) ANTIBODIES FOR ENZYMES OF THE ω-OXIDATION PATHWAY AND METHODS RELATING THERETO

(75) Inventors: Yeyan Zhang, Mason, OH (US); C. Ron Wilson, Loveland, OH (US)

(73) Assignee: Cognis Corporation, Ambler, PA (US)

( * ) Notice: Subject to any disclaimer, the term of this patent is extended or adjusted under 35 U.S.C. 154(b) by 132 days.

(21) Appl. No.: 10/418,820

(22) Filed: Apr. 18, 2003

(65) Prior Publication Data

US 2003/0228641 A1  Dec. 11, 2003

Related U.S. Application Data

(60) Provisional application No. 60/374,066, filed on Apr. 19, 2002.

(51) Int. Cl.
*G01N 33/573* (2006.01)

(52) U.S. Cl. .................. 435/7.4; 435/7.31; 530/387.9; 530/388.26

(58) Field of Classification Search .................. 435/7.1
See application file for complete search history.

(56) References Cited

U.S. PATENT DOCUMENTS 5,866,688 A    2/1999   Kim et al.
6,331,420 B1  12/2001  Wilson et al.

OTHER PUBLICATIONS

Seghezzi et al., "Characterization of a second alkane-inducible cytochrome P450-encoding gene, CYP52A2, from Candida tropicalis" Gene 91991) 106:51-60.*
Backes et al., "Organization of multiple cytochrome P450s with NADPH-cytochrome P450 reductases in membranes" Pharmacology & Therapeutics (2003) 98:221-233.*
Abbas et al., Cellular and Molecular Immunology, fourth edition, (2000) W.B. Saunders Company, pp. 56-58.*
Goldsby et al., Immunology, 5th edition, 2003, W.H. Freeman and Company, p. 141.*

* cited by examiner

*Primary Examiner*—G. R. Ewoldt
*Assistant Examiner*—Michael Szperka
(74) *Attorney, Agent, or Firm*—John F. Daniels

(57) ABSTRACT

The present invention provides antigenic peptides useful for the production of antibodies which selectively bind to an enzyme involved in the ω-oxidation of fatty acids and alkanes to α,ω-dicarboxylic acids in yeast. Antibodies which specifically bind to an enzyme involved in the ω-oxidation of fatty acids and alkanes to α,ω-dicarboxylic acids in yeast are also provided. In addition, methods of producing the subject antibodies, a method of detecting the presence and amount of a specific enzyme involved in the ω-oxidation of fatty acids and alkanes to α,ω-dicarboxylic acids, and a method of monitoring the degree of enzyme induction and/or enzyme stability in a mixture during ω-oxidation of fatty acids and alkanes to α,ω-dicarboxylic acids in yeast, are also provided.

2 Claims, 5 Drawing Sheets

A1   A2   A5   A8   CPR   Ctl

A1   A2   A5   A8   CPR   Ctl 0  4  8  20  27  44  76  124

(A)

(B)

(C)

Figure 5. Strain comparison using Western blot analysis
| Strain | Amplification | Antibody | Western blot |
|---|---|---|---|
| H5343 | | CYP52A2 |  |
| | | CYP52A5 |  |
| | | NCP1B |  |
| HDC28-1 | A2_5A* | CYP52A2 |  |
| | | CYP52A5 |  |
| HDC25 | A2_NCP1B* | NCP1B |  |
| HDC23-3 | CYP52A2A NCP1B | CYP52A2 |  |
| | | NCP1B |  |
| HDC10-2 | NCP1B | NCP1B |  |
| PR 12 | Pox_NCP1B* | NCP1B |  |
| | | NCP1B | @  |
| PA2-21 | Pox_A2* | CYP52A2 | @  |
| PA5- | Pox_A5* | CYP52A5 | @ 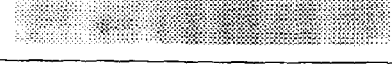 |

SEQUENCE LISTING

<160> NUMBER OF SEQ ID NOS: 32

<210> SEQ ID NO 1
<211> LENGTH: 32
<212> TYPE: DNA
<213> ORGANISM: Candida tropicalis

<400> SEQUENCE: 1
tataccaacc aaccatggcc acacaagaaa tc                32

<210> SEQ ID NO 2
<211> LENGTH: 33
<212> TYPE: DNA
<213> ORGANISM: Candida tropicalis

<400> SEQUENCE: 2
gcagctctcg agttacatct tgacaaagac acc               33

<210> SEQ ID NO 3
<211> LENGTH: 33
<212> TYPE: DNA
<213> ORGANISM: Candida tropicalis

<400> SEQUENCE: 3
caccaccatg gctgtacacg atattatcgc cac               33

<210> SEQ ID NO 4
<211> LENGTH: 31
<212> TYPE: DNA
<213> ORGANISM: Candida tropicalis

<400> SEQUENCE: 4
cacgctcgag ctaatacatc tcaatattgg c                 31

<210> SEQ ID NO 5
<211> LENGTH: 34
<212> TYPE: DNA
<213> ORGANISM: Candida tropicalis

<400> SEQUENCE: 5
gcacaccatg gttgaacaac tcctagaata ttgg              34

<210> SEQ ID NO 6
<211> LENGTH: 34
<212> TYPE: DNA
<213> ORGANISM: Candida tropicalis

<400> SEQUENCE: 6
cggactcgag ctagtcaaac ttgacaatag cacc              34

<210> SEQ ID NO 7
<211> LENGTH: 34
<212> TYPE: DNA
<213> ORGANISM: Candida tropicalis

<400> SEQUENCE: 7
cgctaccatg gtcgatcaga tcttacatta ctgg              34

<210> SEQ ID NO 8
<211> LENGTH: 31
<212> TYPE: DNA
<213> ORGANISM: Candida tropicalis

```
<400> SEQUENCE: 8
cgttctcgag ctatgacatc ttgacgtgtg c                              31

<210> SEQ ID NO 9
<211> LENGTH: 30
<212> TYPE: DNA
<213> ORGANISM: Candida tropicalis

<400> SEQUENCE: 9
aaggccatgg ctatatctag tttgctatcg                                30

<210> SEQ ID NO 10
<211> LENGTH: 29
<212> TYPE: DNA
<213> ORGANISM: Candida tropicalis

<400> SEQUENCE: 10
cggaattctc aagttctagt tcggatgta                                 29

<210> SEQ ID NO 11
<211> LENGTH: 34
<212> TYPE: DNA
<213> ORGANISM: Candida tropicalis

<400> SEQUENCE: 11
cgacggatcc atggctttag acaagttaga tttg                           34

<210> SEQ ID NO 12
<211> LENGTH: 33
<212> TYPE: DNA
<213> ORGANISM: Candida tropicalis

<400> SEQUENCE: 12
ccggaagctt ctaccaaaca tcttcttggt atc                            33

<210> SEQ ID NO 13
<211> LENGTH: 30
<212> TYPE: DNA
<213> ORGANISM: Candida tropicalis

<400> SEQUENCE: 13
aaggccatgg ccgacacaga caccacgacc                                30

<210> SEQ ID NO 14
<211> LENGTH: 30
<212> TYPE: DNA
<213> ORGANISM: Candida tropicalis

<400> SEQUENCE: 14
gtgctcgagt taggcaaagt tggtcttgta                                30

<210> SEQ ID NO 15
<211> LENGTH: 17
<212> TYPE: PRT
<213> ORGANISM: Candida tropicalis

<400> SEQUENCE: 15

Tyr Ala Ala His Arg Asn Pro Ala Val Tyr Gly Lys Asp Ala Leu Glu
 1               5                  10                  15

Phe
```

-continued

<210> SEQ ID NO 16
<211> LENGTH: 23
<212> TYPE: PRT
<213> ORGANISM: Candida tropicalis

<400> SEQUENCE: 16

Glu Leu Leu Lys Lys Ser Asp Gly Thr Leu Ile Asp Phe Thr Leu
1               5                   10                  15

Gln Arg Ile His Asp Leu Asp
            20

<210> SEQ ID NO 17
<211> LENGTH: 16
<212> TYPE: PRT
<213> ORGANISM: Candida tropicalis

<400> SEQUENCE: 17

Ala Thr His Arg Asp Pro Ser Ile Tyr Gly Ala Asp Ala Asp Val Phe
1               5                   10                  15

<210> SEQ ID NO 18
<211> LENGTH: 18
<212> TYPE: PRT
<213> ORGANISM: Candida tropicalis

<400> SEQUENCE: 18

Gly Leu Trp Asn Asn Lys Tyr Ile Val Arg Asp Pro Lys Tyr Lys Thr
1               5                   10                  15

Thr Gly

<210> SEQ ID NO 19
<211> LENGTH: 25
<212> TYPE: PRT
<213> ORGANISM: Candida tropicalis

<400> SEQUENCE: 19

Gln Lys Gly Glu Ala Val Ser Tyr Gly Ile Asn Ser Thr His Leu Asp
1               5                   10                  15

Pro Val Tyr Tyr Gly Pro Asp Ala Ala
            20                  25

<210> SEQ ID NO 20
<211> LENGTH: 23
<212> TYPE: PRT
<213> ORGANISM: Candida tropicalis

<400> SEQUENCE: 20

Gln Phe Lys Lys Glu Gly Arg Ala Gln Glu Tyr Asn Asp Tyr Lys Phe
1               5                   10                  15

Asp His Ser Lys Asn Pro Ser
            20

<210> SEQ ID NO 21
<211> LENGTH: 19
<212> TYPE: PRT
<213> ORGANISM: Candida tropicalis

<400> SEQUENCE: 21

Tyr Asp Glu Lys Leu Gly Ile Pro Thr Pro Asn Glu Ile Pro Gly Arg
1               5                   10                  15

Glu Asn Phe

```
<210> SEQ ID NO 22
<211> LENGTH: 15
<212> TYPE: PRT
<213> ORGANISM: Candida tropicalis

<400> SEQUENCE: 22

Ala Tyr Val Val Tyr Lys Thr His Arg Leu Glu Glu Tyr Tyr Gly
1               5                   10                  15

<210> SEQ ID NO 23
<211> LENGTH: 15
<212> TYPE: PRT
<213> ORGANISM: Candida tropicalis

<400> SEQUENCE: 23

Gln Met Phe Glu Thr Val Ser Ser Asp Pro Gly Leu Glu Tyr Pro
1               5                   10                  15

<210> SEQ ID NO 24
<211> LENGTH: 17
<212> TYPE: PRT
<213> ORGANISM: Candida tropicalis

<400> SEQUENCE: 24

Ala Asn Phe Ala Asp Glu Val Phe Asp Glu Tyr Pro Asn His Thr Phe
1               5                   10                  15

Tyr

<210> SEQ ID NO 25
<211> LENGTH: 17
<212> TYPE: PRT
<213> ORGANISM: Candida tropicalis

<400> SEQUENCE: 25

Glu Glu Ile Gly Tyr Asp Thr Lys Asp Met Ser Glu Glu Arg Arg
1               5                   10                  15

Phe

<210> SEQ ID NO 26
<211> LENGTH: 24
<212> TYPE: PRT
<213> ORGANISM: Candida tropicalis

<400> SEQUENCE: 26

Phe Thr His Val Gln Arg Asp Gly Trp Leu Gly Phe Lys Phe Gly Arg
1               5                   10                  15

Glu Phe Leu Lys Ala Lys Ser Ala
                20

<210> SEQ ID NO 27
<211> LENGTH: 22
<212> TYPE: PRT
<213> ORGANISM: Candida tropicalis

<400> SEQUENCE: 27

Arg Lys Asp Glu Val Val Gln Tyr Ser Ile Ser Ala Thr Gln Thr Asn
1               5                   10                  15

Pro Ala Tyr Tyr Gly Ala
                20

<210> SEQ ID NO 28
<211> LENGTH: 23
<212> TYPE: PRT
```

<213> ORGANISM: Candida tropicalis

<400> SEQUENCE: 28

Arg Phe His Asp Asn Glu Asp Thr Phe Ser Ser Tyr Ala Phe Gly Asn
1               5                   10                  15

His Val Val Phe Thr Arg Asp
            20

<210> SEQ ID NO 29
<211> LENGTH: 20
<212> TYPE: PRT
<213> ORGANISM: Candida tropicalis

<400> SEQUENCE: 29

Leu Asn Gly Val Tyr Ile Arg Thr Arg Thr Leu Asn Gly Val Tyr Ile
1               5                   10                  15

Arg Thr Arg Thr
            20

<210> SEQ ID NO 30
<211> LENGTH: 20
<212> TYPE: PRT
<213> ORGANISM: Candida tropicalis

<400> SEQUENCE: 30

Ser Val Lys Arg Phe Glu Ser Ala Pro His Pro Gln Asn Lys Thr Leu
1               5                   10                  15

Val Asn Arg Ala
            20

<210> SEQ ID NO 31
<211> LENGTH: 22
<212> TYPE: PRT
<213> ORGANISM: Candida tropicalis

<400> SEQUENCE: 31

Glu Tyr Ala Glu Gly Asp Asp Gly Thr Gly Thr Leu Asp Glu Asp Phe
1               5                   10                  15

Met Ala Trp Lys Asp Asn
            20

<210> SEQ ID NO 32
<211> LENGTH: 23
<212> TYPE: PRT
<213> ORGANISM: Candida tropicalis

<400> SEQUENCE: 32

Ser Glu Asp Lys Ala Ala Glu Leu Val Lys Ser Trp Lys Val Gln Asn
1               5                   10                  15

Arg Tyr Gln Glu Asp Val Trp
            20

ANTIBODIES FOR ENZYMES OF THE ω-OXIDATION PATHWAY AND METHODS RELATING THERETO

CROSS REFERENCE TO RELATED APPLICATIONS

The present invention claims benefit of U.S. Provisional Application Ser. No. 60/374,066, filed Apr. 19, 2002, which application is incorporated by reference herein.

STATEMENT REGARDING FEDERALLY SPONSORED RESEARCH OR DEVELOPMENT

This invention was funded, at least in part, under a grant from the Department of Commerce, NIST-ATP Cooperative Agreement Number 70NANB8H4033. The Government may therefore have certain rights in the invention.

FIELD OF THE INVENTION

The present invention relates to generation of antibodies specific for selected proteins and methods of using such antibodies. More particularly, the invention relates to generation of antibodies specific for enzymes of the ω-hydroxylase complex and methods of using those antibodies.

BACKGROUND OF THE INVENTION

Aliphatic dioic acids are versatile chemical intermediates useful as raw materials for the preparation of perfumes, polymers, adhesives, and macrolid antibiotics. Long chain α,ω-dicarboxylic acids may be chemically synthesized. Synthesis is difficult and most methods result in mixtures containing shorter chain lengths, requiring additional, extensive purification steps. Several strains of yeasts are known to excrete α,ω-dicarboxylic acids as a byproduct when cultured on alkanes or fatty acids as the carbon source. In particular, yeast belonging to the Genus Candida, such as *C. albicans, C. cloacae, C. guillermondii, C. intermedia, C. lipolytica, C. maltosa, C. parapsilosis* and *C. zeylenoides* are known to produce such dicarboxylic acids (*Agr. Biol. Chem.* 35: 2033–2042 (1971)). Also, various strains of *C. tropicalis* are known to produce dicarboxylic acids ranging in chain lengths from $C_{11}$ through $C_{18}$ (Okino et al., B M Lawrence, B D Mookherjee and B J Willis (eds), in *Flavors and Fragrances: A World Perspective*, Proceedings of the 10$^{th}$ International Conference of Essential Oils, Flavors and Fragrances, Elsevier Science Publishers BV Amsterdam (1988)), and are the basis of several patents as reviewed by Bühler and Schindler, in *Aliphatic Hydrocarhons in Biotechnology*, H. J. Rehm and G. Reed (eds), Vol. 169, Verlag Chemie, Weinheim (1984).

Studies of the biochemical processes by which yeasts metabolize alkanes and fatty acids have revealed three types of oxidation reactions: α-oxidation of alkanes to alcohols; ω-oxidation of fatty acids to α,ω-dicarboxylic acids; and the degradative β-oxidation of fatty acids ultimately to $CO_2$ and water. Various strains of the yeast *C. tropicalis* are known to produce dicarboxylic acids ranging in chain lengths from $C_{11}$ through $C_{18}$ as a byproduct when cultured on alkanes or fatty acids as the carbon source (Okino et al., B M Lawrence, B D Mookherjee and B J Willis (eds.), in *Flavors and Fragrances: A World Perspective*. Proceedings of the 10$^{th}$ International Conference of Essential Oils, Flavors and Fragrances, Elsevier Science Publishers BV Amsterdam (1988)), and are the basis of several patents as reviewed by Bühler and Schindler, in *Aliphatic Hydrocarhons in Biotechnology*, H. J. Rehm and G. Reed (eds), Vol. 169, Verlag Chemie, Weinheim (1984).

In *C. tropicalis,* the first step in the ω-oxidation pathway is catalyzed by a membrane-bound enzyme complex (ω-hydroxylase complex) including a cytochrome P450 monooxygenase and a NADPH cytochrome reductase. This hydroxylase complex is responsible for the primary oxidation of the terminal methyl group to an alcohol in alkanes and fatty acids (Gilewicz et al., *Can. J. Microbiol.* 25:201 (1979)). The resultant alcohol is then converted to an aldehyde by fatty alcohol oxidase (FAO) and then to the dicarboxylic acid by an aldehyde dehydrogenase.

The genes that encode the cytochrome P450 and NADPH reductase components of the complex have previously been identified as P450ALK and P450RED respectively, and have also been cloned and sequenced (see e.g., Sanglard et al., *Gene* 76:121–136 (1989)). P450ALK has also been designated P450ALK1. More recently, ALK genes have been designated by the symbols CYP and RED genes have been designated by the symbols CPR and NCP. See, e.g., Nelson, *Pharmacogenetics* 6(1):1–42 (1996), which is incorporated herein by reference. See also Ohkuma et al., *DNA and Cell Biology* 14:163–173 (1995), Seghezzi et al., *DNA and Cell Biology*, 11:767–780 (1992) and Kargel et al., *Yeast* 12:333–348 (1996), each incorporated herein by reference. For example, P450ALK is also designated CYP52 according to the nomenclature of Nelson, supra. A small number of fatty alcohol oxidases have been described in the scientific literature in various yeasts, examples of which are *Candida tropicalis,* Kemp et al., *Appl. Microbiol. Biotechnol,* 29:370–374 (1988), *Appl. Microbiol. Biotechnol.* 34:441–445 (1991), Dickinson F M, Wadforth C, *Biochem. J.* 282:325–331 (1992), Vanhanen et al., *J. Biol. Chem.* 275:4445–4452 (2000), *Candida maltosa,* Blasig et al., *Appl. Microbiol. Biotechnol.* 28:589–597 (1988), Mauersberger et al., *Appl. Microbiol. Biotechnol* 37:66–73 (1992), *Candida cloacae,* Vanhanen et al., *J. Biol. Chem.* 275: 4445–4452 (2000), *Candida (Torulopsis) hombicola,* Hommel et al. *FEMS Microbiol. Lett.* 70:183–186 (1990), and *Candida (Torulopsis) apicola,* Hommel et al., *Appl. Microbiol. Biotechnol.* 40:729–734 (1994).

FAO proteins and the corresponding coding sequences from *Candida tropicalis* are described in copending application Ser. No. 10/418,819 filed Apr. 18, 2003, originally filed as Provisional Application Ser. No. 60/374,021 on Apr. 19, 2002, which applications are incorporated by reference herein as if fully set forth.

Cytochromes P450 (P450s) are terminal monooxidases of the multicomponent enzyme system described above. In some instances, a second electron carrier, cytochrome b5 (CYTb5) and its associated reductase is involved in the ω-oxidation pathway. P450s comprise a superfamily of proteins which exist widely in nature having been isolated from a variety of organisms, e.g., various mammals, fish, invertebrates, plants, mollusks, crustaceans, lower eukaryotes and bacteria (Nelson, supra). First discovered in rodent liver microsomes as a carbon-monoxide binding pigment as described, e.g., in Garfinkel, *Arch. Biochem. Biophys.* 77:493–509 (1958), which is incorporated herein by reference, P450s were later named based on their absorption at 450 nm in a reduced-CO coupled difference spectrum as described, e.g., in Omura et al., *J. Biol. Chem.* 239:2370–2378 (1964), which is incorporated herein by reference.

P450 families are assigned based upon protein sequence comparisons. Notwithstanding a certain amount of heterogeneity, a practical classification of P450s into families can be obtained based on deduced amino acid sequence similarity. P450s with amino acid sequence similarity of between about 40–80% are considered to be in the same family, with sequences of about >55% belonging to the same subfamily. Those with sequence similarity of about <40% are generally listed as members of different P450 gene families (Nelson, supra). A value of about >97% is taken to indicate allelic variants of the same gene, unless proven otherwise based on catalytic activity, sequence divergence in non-translated regions of the gene sequence, or chromosomal mapping.

Metabolic pathways can be manipulated in an attempt to increase or decrease the production of various products or by-products. One example is the manipulation of the ω-oxidation pathway to produce greater amounts of dicarboxylic acids. See, e.g., U.S. Pat. No. 6,331,420, which discloses novel genes encoding certain cytochrome P450 and NADPH reductase enzymes of the ω-hydroxylase complex in yeast *Candida tropicalis*, and a method of quantitating the expression of genes. It can be helpful to monitor the levels of enzymes catalyzing these reactions, especially where the metabolic pathways are manipulated in an attempt to affect the production of certain products or by-products.

Immunoassays are frequently used in evaluating protein induction, expression and degradation. Since immunoassays involve interactions between antibodies and their targets, it is important to generate antibodies with appropriate antigen binding sites. Thus, purified proteins are generally required to generate such antibodies. It may be difficult however, to fashion immunoassays for detection of and/or monitoring membrane-bound proteins such as the enzymes involved in the ω-oxidation of fatty acids and alkanes to α,ω-dicarboxylic acids for several reasons. First, not all of these enzymes are induced at all times and their presence may be fleeting. It is also difficult to obtain pure samples of these enzymes, since different enzymes involved in the ω-oxidation of fatty acids and alkanes to α,ω-dicarboxylic acids may have the same or similar activity and similar molecular weights. Conversely, notwithstanding the fact that certain enzymes have a high degree of homology, such enzymes may have very different activities. In the absence of suitable alternatives, peptide sequencing may be required to verify the identity of the purified enzymes involved in the ω-oxidation pathway. Moreover, antibodies generated in response to one particular protein involved in the ω-oxidation of fatty acids and alkanes to α,ω-dicarboxylic acids can cross react against other proteins involved in the ω-oxidation of fatty acids and alkanes to α,ω-dicarboxylic acids. Accordingly, there remains a need for antigenic peptides useful for the production of antibodies reactive against enzymes involved in the ω-oxidation of fatty acids and alkanes to α,ω-dicarboxylic acids. Methods of using the generated antibodies in order to monitor enzyme levels and reactions involved in the ω-oxidation of fatty acids and alkanes to α,ω-dicarboxylic acids are also needed.

SUMMARY OF THE INVENTION

The present invention provides antigenic peptides useful for the production of antibodies which selectively bind to an enzyme involved in the ω-oxidation of fatty acids and alkanes to α,ω-dicarboxylic acids in yeast. Preferred antigenic peptides are those having the amino acid sequences as set forth in SEQ ID NO:15, SEQ ID NO:16, SEQ ID NO:17, SEQ ID NO:18, SEQ ID NO:19, SEQ ID NO:20, or SEQ ID NO:31, or an analog, derivative or immunologically active fragment thereof.

Antibodies which specifically bind to an enzyme involved in the ω-oxidation of fatty acids and alkanes to α,ω-dicarboxylic acids in yeast are also provided. Preferably, a subject antibody selectively binds to a peptide having an amino acid sequence as set forth in at least one of SEQ ID NO:15, SEQ ID NO:16, SEQ ID NO:17, SEQ ID NO:18, SEQ ID NO:19, SEQ ID NO:20, or SEQ ID NO:31 or an analog, derivative or immunologically active fragment thereof. A subject antibody may be monoclonal or polyclonal.

A method for producing antibodies which selectively bind to an enzyme involved in the ω-oxidation of fatty acids and alkanes to α,ω-dicarboxylic acids in yeast is also provided. The method comprises: (a) inoculating an animal with an antigenic peptide which selectively binds to an enzyme involved in the ω-oxidation of fatty acids and alkanes to α,ω-dicarboxylic acids in yeast; (b) recovering antibodies from serum of the animal; and (c) screening the recovered antibodies to determine which antibodies selectively bind to an enzyme involved in the ω-oxidation of fatty acids and alkanes to α,ω-dicarboxylic acids in yeast. Preferably, the antigenic peptide has an amino acid sequence as set forth in at least one of SEQ ID NO:15, SEQ ID NO:16, SEQ ID NO:17, SEQ ID NO:18, SEQ ID NO:19, SEQ ID NO:20, or SEQ ID NO:31, or an analog, derivative, or immunologically active fragment thereof. Preferably, an enzyme involved in the ω-oxidation of fatty acids and alkanes to α,ω-dicarboxylic acids in yeast is at least one of cytochrome P450 monooxygenase, cytochrome P450 reductase, cytochrome b5, and fatty alcohol oxidase (FAO).

Also provided is a method for producing antibodies which selectively bind to an enzyme involved in the ω-oxidation of fatty acids and alkanes to α,ω-dicarboxylic acids in yeast. The method comprises: (a) immunizing an animal with an antigenic peptide which selectively binds to an enzyme involved in the ω-oxidation of fatty acids and alkanes to α,ω-dicarboxylic acids in yeast; (b) obtaining spleen cells from the immunized animal; (c) fusing the spleen cells with myeloma cells or transformed cells capable of replicating indefinitely in culture to produce hybridomas; (d) culturing the resultant hybridomas; and (e) screening the cultured hybridomas for production of antibodies which selectively bind to an enzyme involved in the ω-oxidation of fatty acids and alkanes to α,ω-dicarboxylic acids in yeast. Preferably, the antigenic peptide has an amino acid sequence as set forth in at least one of SEQ ID NO:15, SEQ ID NO:16, SEQ ID NO:17, SEQ ID NO:18, SEQ ID NO:19, SEQ ID NO:20, or SEQ ID NO:31 or an analog, derivative, or immunologically active fragment thereof. The enzyme involved in the ω-oxidation of fatty acids and alkanes to α,ω-dicarboxylic acids in yeast is preferably at least one of cytochrome P450 monooxygenase, cytochrome P450 reductase, cytochrome b5, and fatty alcohol oxidase (FAO).

In yet another aspect of the invention, there is provided a method of detecting the presence and amount of a specific enzyme involved in the ω-oxidation of fatty acids and alkanes to α,ω-dicarboxylic acids in a mixture suspected of having said enzyme. The method comprises generating an antibody which specifically binds to an enzyme involved in the ω-oxidation of fatty acids and alkanes to α,ω-dicarboxylic acids, incubating the antibody with the mixture for a time and under conditions sufficient to allow binding of the antibody to the specific ω-hydroxylase enzyme, and detecting the enzyme-antibody complex. Preferably, the antigenic peptide has an amino acid sequence as set forth in at least one of SEQ ID NO:15, SEQ ID NO:16, SEQ ID NO:17, SEQ ID NO:18, SEQ ID NO:19, SEQ ID NO:20, or SEQ ID NO:31, or an analog, derivative, or immunologically active fragment thereof. In addition, the enzyme involved in the ω-oxidation of fatty acids and alkanes to α,ω-dicarboxylic acids in yeast is preferably at least one of cytochrome P450 monooxygenase, cytochrome P450 reductase, cytochrome b5, or fatty alcohol oxidase (FAO).

A method of monitoring the degree of enzyme induction and/or enzyme stability in a mixture during ω-oxidation of fatty acids or alkanes to α,ω-dicarboxylic acids is also provided. The method comprises generating an antibody which specifically binds to an enzyme involved in the ω-oxidation of fatty acids and alkanes to α,ω-dicarboxylic acids in yeast; incubating the antibody with the mixture for a time and under conditions sufficient to allow binding of the antibody to an enzyme involved in the ω-oxidation of fatty acids and alkanes to α,ω-dicarboxylic acids, detecting the enzyme-antibody complex, and correlating the amount of enzyme-antibody complex with a degree of enzyme induction and/or enzyme stability. Preferably, the antigenic peptide has an amino acid sequence as set forth in at least one of SEQ ID NO:15, SEQ ID NO:16, SEQ ID NO:17, SEQ ID NO:18, SEQ ID NO:19, SEQ ID NO:20, or SEQ ID NO:31, or an analog, derivative, or immunologically active fragment thereof. The enzyme involved in the ω-oxidation of fatty acids and alkanes to α,ω-dicarboxylic acids in yeast is preferably at least one of cytochrome P450 monooxygenase, cytochrome P450 reductase, cytochrome b5, or fatty alcohol oxidase (FAO).

BRIEF DESCRIPTION OF THE DRAWINGS

FIG. 5 shows results of Western blots using different antibodies against different enzymes of omega-hydroxylase complex in different yeast strains.

DETAILED DESCRIPTION OF THE INVENTION

Figure 1:
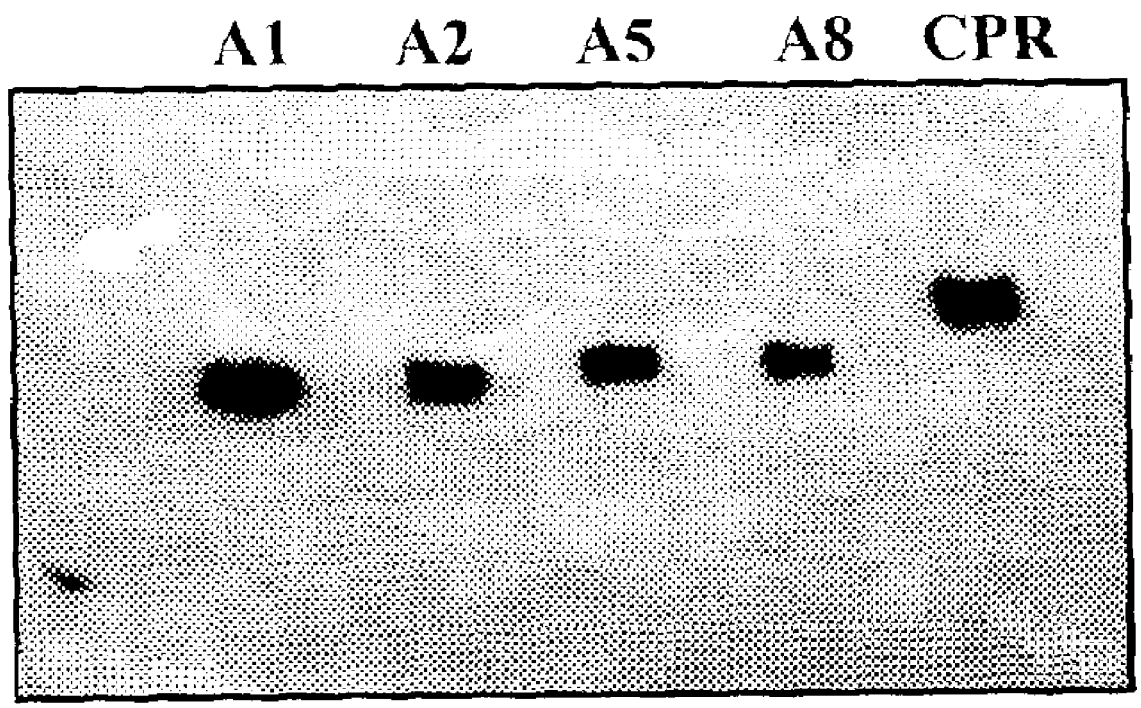
FIG. 1 shows purified recombinant His-tagged proteins on SDS-PAGE.

The present invention provides antigenic peptides useful for the production of antibodies which antibodies selectively bind to different enzymes involved in the ω-oxidation of fatty acids and alkanes to α,ω-dicarboxylic acids in yeast. In accordance with the present invention, synthetic antigenic peptides may be used to elicit antibodies which bind to a selected protein involved in the ω-oxidation of fatty acids and alkanes to α,ω-dicarboxylic acids without the need for obtaining a purified sample of the selected protein. Amino acid sequences of exemplary peptides which may be used to elicit antibody production include but are not limited to those peptides set forth in Table 1. In addition to those peptides listed in Table 1, other peptides derived from amino acid sequences of different enzymes involved in the ω-oxidation of fatty acids and alkanes to α,ω-dicarboxylic acids may be obtained and tested as suitable antigenic peptides for antibody production in accordance with the present invention.

The present invention also provides antibodies which selectively bind to different enzymes involved in the ω-oxidation of fatty acids and alkanes to α,ω-dicarboxylic acids in yeast. Methods of producing such antibodies are also provided. Preferably, a subject antibody selectively binds to a specific enzyme involved in the ω-oxidation of fatty acids and alkanes to α,ω-dicarboxylic acids and exhibits little cross reactivity with other enzymes of the ω-oxidation pathway of yeast. In a most preferred embodiment, a subject antibody selectively binds to one particular enzyme involved in the ω-oxidation of fatty acids and alkanes to α,ω-dicarboxylic acids and does not bind to any other enzyme involved in the ω-oxidation of fatty acids and alkanes to α,ω-dicarboxylic acids.

The subject antibodies are useful for detecting and monitoring the degree of enzyme induction and/or enzyme stability during ω-oxidation of fatty acids or alkanes to dicarboxylic acids. The antibodies may also be used to verify the effects of genetic modifications to genes encoding the ω-hydroxylase enzymes. Preferably, antibodies are generated which specifically bind to cytochrome P450 monoxygenase, cytochrome P450 reductase (CPR) cytochrome b5 (CYTb5), and fatty alcohol oxidase (FAO).

Antibodies of the present invention may be polyclonal antibodies produced by an animal after injecting the animal with antigenic peptides (and suitable carriers, if any) derived from an enzyme involved in the ω-oxidation of fatty acids and alkanes to α,ω-dicarboxylic acids, recovering antibodies from serum of the animal, and screening the antibodies to determine those that are capable of binding to an enzyme involved in the ω-oxidation of fatty acids and alkanes to α,ω-dicarboxylic acids. Monoclonal antibodies specific to different enzymes in the ω-oxidation pathway may also be generated in accordance with the present invention. In certain embodiments, polyclonal or monoclonal antibodies according to the present invention are produced in response to the antigenic peptides listed in Table 1. In other embodiments, polyclonal or monoclonal antibodies according to the present invention are generated which bind to other antigenic determinants of yeast cytochrome P450, yeast cytochrome P450 reductase, yeast cytochrome b5, or yeast fatty alcohol oxidase.

Animals, for example, mammals such as mice, goats, rats, sheep or rabbits, or other animals such as poultry, e.g., chickens, can be inoculated with a subject antigenic peptide conjugated with a suitable carrier protein to produce polyclonal antibodies. Immunoglobulins are purified from the serum obtained from the immunized animals. These immunoglobulins can then be utilized in immunoassays to detect the presence of enzymes of the ω-oxidation pathway in a sample and/or to monitor the fermentation process for enzymes critical for bioconversion.

Monoclonal antibodies may also be prepared and used in immunoassays in order to detect an enzyme of the ω-oxidation pathway using techniques which are well-known in the art such those described in Kohler and Milstein (1975) *Nature* 256:495–497, which is incorporated by reference herein as if fully set forth. For example, an animal may be immunized with an antigenic peptide including but not limited to those listed in Table 1 and spleen cells from the immunized animal obtained. The antibody-secreting lymphocytes are then fused with myeloma cells or transformed cells which are capable of replicating indefinitely in cell culture. Resulting hybridomas may be cultured and the resulting colonies screened for the production of the desired monoclonal antibodies. Antibody producing colonies are grown either in vivo or in vitro in order to produce large amounts of antibody.

Mammalian lymphocytes can be immunized by in vivo immunization of the animal, e.g., a mouse, with an antigenic peptide of the present invention. Such immunizations may be repeated as necessary at intervals of up to several weeks in order to obtain a sufficient titer of antibodies. After the last antigen boost, the animal is sacrificed and spleen cells removed.

Fusion with mammalian myeloma cell or other fusion partners capable of replicating indefinitely in cell culture is effected by standard and well-known techniques, for example, by using polyethylene glycol (PEG) or other fusing agents such as described in Milstein and Kohler (1976) Eur. J. Immunol. 6:511, which is incorporated by reference herein as if fully set forth. Such an immortal cell line is preferably murine, but may also be derived from cells of other mammalian species such as rats and human. Preferably the cell line is deficient in enzymes necessary for the utilization of certain nutrients, is capable of rapid growth and has a good fusion capability. Such cell lines are known to those skilled in the art.

The present invention further provides an immunoassay using a polyclonal or monoclonal antibody specific against an enzyme involved in the ω-oxidation of fatty acids and alkanes to α,ω-dicarboxylic acids to detect the presence and amount of the enzyme in a mixture which is suspected of having the enzyme. The antibody is added to the mixture, which is analyzed to determine whether or not the antibody is bound to the enzyme to form an enzyme-antibody complex. In one embodiment, in order to detect the presence of the enzyme-antibody complex, a labeled binding partner of the enzyme-antibody complex is added to the mixture to form a labeled complex, and the mixture is analyzed to determine the presence of the labeled complex.

In another embodiment, the degree of enzyme induction and/or enzyme stability during ω-oxidation of fatty acids or alkanes to dicarboxylic acids is monitored in a sample by determining whether or not a polyclonal or monoclonal antibody directed to an enzyme involved in the ω-oxidation of fatty acids and alkanes to α,ω-dicarboxylic acids is bound to such an enzyme. The amount of enzyme and the amount of dicarboxylic acids in the sample can be monitored to provide information concerning induction of the enzyme in response to substrates and other conditions in fermentation media and their correspondence to efficiency of production of the dicarboxylic acids. The information may be used to manipulate the amount of ω-oxidation pathway enzyme produced and to increase the amount of dicarboxylic acids produced.

The term "immunoglobulin" as used herein is intended to encompass whole immunoglobulin molecules or molecules that contain immunologically active portions of whole immunoglobulin molecules and includes Fab, F(ab')$_2$, scFv, Fv, heavy chain variable regions and light chain variable regions. The terms "immunoglobulin" and "antibody" are used interchangeably herein.

In the present invention, the synthetic antigenic peptide is purified and prepared for inoculating by known techniques. The antigenic peptides can be prepared, if desired, by standard solid phase or other peptide synthesis methods. Peptides may be conjugated to a carrier molecule, e.g., haptens, to assist immune system recognition.

According to the present invention, the amino acid sequences of peptides deduced from the DNA sequences of the genes encoding enzymes involved in the ω-oxidation of fatty acids and alkanes to α,ω-dicarboxylic acids are analyzed for their potential antigenicity, as determined by their hydrophilicity profile and surface probability. Regions of peptide sequences displaying good antigenicity and likely representing linear epitopes are selected. To ensure that at least one set of specific antibodies are produced for each enzyme, at least two peptides (one from the C-terminus and one from the N-terminus) may be designed per enzyme for antibody generation. In preferred embodiments, the target enzymes are CYP52A1, CYP52A2, CYP52A5, CYP52A8, CPR and CYTb5 and FAO1 and FAO2. The nucleotide sequences and corresponding amino acid sequences of CYP52A1, CYP52A2, CYP52A8, and CYP genes are disclosed in U.S. Pat. No. 6,331,420. The nucleotide sequence for CYTb5 is disclosed in copending U.S. patent application Ser. No. 09/912,16 1.Nucleotide sequences for FAO1 and FAO2 are provided in copending U.S. patent application Ser. No. 10/418,819 originally filed as U.S. Provisional Application Ser. No. 60/374,021 on Apr. 19, 2002. Exemplary amino acid sequences of synthesized peptides that correspond to the aforementioned enzymes are set forth in Table 1 (SEQ ID NOs: 15–32). Preferred antigenic peptides are those having amino acid sequences as set forth in SEQ ID NOs: 15, 16, 17, 18, 19, 20, or 31.

Structurally related amino acid sequences may be substituted for the disclosed sequences set forth in SEQ ID NOs: 15–32 in practicing the present invention. Amino acid insertional derivatives of the proteins and peptides of the present invention include amino and/or carboxyl terminal fusions as well as intra-sequence insertions of single or multiple amino acids. Insertional amino acid sequence variants are those in which one or more amino acid residues are introduced into a predetermined site in a subject antigenic peptide although random insertion is also possible with suitable screening of the resulting product. Deletional variants may be made by removing one or more amino acids from the sequence of a subject peptide. Substitutional amino acid variants are those in which at least one residue in the sequence has been removed and a different residue inserted in its place. Typical substitutions are those made in accordance with the following Table 1:

TABLE 1

Suitable residues for amino acid substitutions

| Original Residue | Exemplary Substitutions |
| --- | --- |
| Ala (A) | Ser |
| Arg (R) | Lys |
| Asn (N) | Gln; His |
| Asp (D) | Glu |
| Cys (C) | Ser |
| Gln (Q) | Asn |
| Glu (E) | Asp |
| Gly (G) | Pro |
| His (H) | Asn; Gln |
| Ile (I) | Leu; Val |
| Leu (L) | Ile; Val |
| Lys (K) | Arg; Gln; Glu |

TABLE 1-continued

Suitable residues for amino acid substitutions

| Original Residue | Exemplary Substitutions |
| --- | --- |
| Met (M) | Leu; Ile |
| Phe (F) | Met; Leu; Tyr |
| Ser (S) | Thr |
| Thr(T) | Ser |
| Trp (W) | Tyr |
| Tyr (Y) | Trp; Phe |
| Val (V) | Ile; Leu |

When a subject antigenic peptide is derivatised by amino acid substitution, the amino acids are generally replaced by other amino acids having like properties such as hydrophobicity, hydrophilicity, electronegativety, bulky side chains and the like. As used herein, the terms "derivative", "analogue", "immunologically active fragment", "portion" and "like molecule" refer to a subject antigenic peptide having an amino acid sequence as set forth in SEQ ID NOs: 15–32 and having an amino acid substitution, insertion, addition, or deletion, as long as said derivative, analogue, fragment, portion, or like molecule retains the ability to selectively bind to an enzyme involved in the ω-oxidation of fatty acids and alkanes to α,ω-dicarboxylic acids.

The synthetic peptides of the present invention may be synthesized by a number of known techniques. For example, the peptides may be prepared using the solid-phase technique initially described by Merrifield (1963) in *J. Am. Chem. Soc.* 85:2149–2154. Other peptide synthesis techniques may be found in M. Bodanszky et al. *Peptide Synthesis,* John Wiley and Sons, 2d Ed., (1976) and other references readily available to those skilled in the art. A summary of polypeptide synthesis techniques may be found in J. Sturart and J. S. Young, *Solid Phase Peptide Synthesis,* Pierce Chemical Company, Rockford, Ill., (1984). Peptides may also be synthesized by solution methods as described in *The Proteins,* Vol. II, 3d Ed., Neurath, H. et al., Eds., pp. 105–237, Academic Press, New York, N.Y. (1976). Appropriate protective groups for use in different peptide syntheses are described in the texts listed above as well as in J. F. W. McOmie, *Protective Groups in Organic Chemistry,* Plenum Press, New York, N.Y. (1973). The peptides of the present invention may also be prepared by chemical or enzymatic cleavage from larger portions of a subject enzyme involved in the ω-oxidation of fatty acids and alkanes to α,ω-dicarboxylic acids protein or from such full length proteins.

Additionally, the subject peptides of the present invention may be prepared by recombinant DNA techniques. For most amino acids used to build proteins, more than one coding nucleotide triplet (codon) can code for a particular amino acid residue. This property of the genetic code is known as redundancy. Therefore, a number of different nucleotide sequences may code for a particular antigenic peptide.

The term "antigenic peptide" refers to a protein or a fragment of a protein that is antigenic and used to immunize a host animal to produce antibodies. An antigenic peptide used to immunize an animal (e.g., a mouse, goat, rat, sheep, rabbit, or chicken) can be obtained from the translation of RNA, or synthesized chemically, and can optionally be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal and produce antibodies according to standard protocols.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody. Methods for selection of appropriate epitopes, such as those near the C-terminus or in hydrophilic regions are well described in the art. (See, e.g., Ausubel, F. M., et al. (1995), Current Protocols in Molecular Biology, John Wiley & Sons, New York, N.Y., ch. 11.)

A subject peptide may be substantially purified using common techniques known to those skilled in the art such as polyacrylamide gel electrophoresis (PAGE; see, e.g., Harrington, M. G. (1990) Methods Enzymol., 182:488–495), and size-exclusion chromatography. Other purification techniques, such as immunoaffinity chromatography (using antibodies specific for the antigenic peptide), may also be used. An immunoaffinity column is constructed, e.g., by covalently coupling the antibody to an activated chromatographic resin, such as CNBr-activated SEPHAROSE (Amersham Pharmacia Biotech). After the coupling, the resin is blocked and washed according to the manufacturer's instructions. Media containing the antigenic peptide are passed over the immunoaffinity column, and the column is washed under conditions that allow the preferential absorbance of the antigenic peptide (e.g., high ionic strength buffers in the presence of detergent). The column is eluted under conditions that disrupt antibody/antigenic peptide binding (e.g., a buffer of pH 2 to pH 3, or a high concentration of a chaotrope, such as urea or thiocyanate ion), and the antigenic peptide is collected.

Selected antigenic peptides are injected into at least one suitable animal, for example, sheep, to elicit an immune response for antibody generation. The animal is maintained under conditions whereby antibodies reactive with the components of the antigenic peptide are produced. Blood is collected from the animal to determine if antibodies are produced, the antisera is tested for response to the antigenic peptide, and reboosting or antigenic peptide redesign is undertaken, as needed.

Antisera showing good responses to a specific antigenic peptide may be used as whole sera or are IgG fractionated and tested for responses to other antigenic peptides. The whole sera or fractions that are specific to the selected antigenic peptide are then validated against whole, purified recombinant enzymes or fragments thereof, which proteins may be produced as described below.

The whole proteins or fragments thereof from which a subject antigenic peptide is derived, may be prepared by methods familiar to those skilled in the art such as by cloning into an appropriate expression vector followed by expression in a suitable host cell. The general techniques used in the present invention, especially in constructing expression vectors, transforming cells and growing cells and the like are known in the art and laboratory manuals describing such techniques are widely available. See e.g. Sambrook et al. (1989) *Molecular Cloning: A Laboratory Manual,* 2nd Edition, Cold Spring Harbor Press, Cold Spring Harbor, N.Y. The relevant enzyme or fragment thereof, may also be generated by direct amplification of corresponding coding sequence via PCR, followed by standard recombinant procedures and expression in a suitable host cell. Primers for use in PCR may be synthetic oligonucleotides prepared on an automated oligonucleotide synthesizer such as an ABI DNA synthesizer available from Perkin-Elmer Corporation. In addition, oligonucleotides may be purchased from commercial manufacturers, for example, from Synthetic Genetics (San Diego, Calif.).

Coding sequences including fragments thereof such as an oligonucleotide may be included in any one of a variety of expression vectors following the manufacturer's protocol. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures deemed to be within the scope of those skilled in the art, which can include insertion of the DNA into an appropriate restriction endonuclease site(s) or cloning the DNA sequence into the expression vectors using high fidelity polymerase chain reaction. Oligonucleotide coding sequences can be amplified and isolated by standard recombinant procedures or by polymerase chain reaction. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or tetracycline or ampicillin resistance in *E. coli*. In a preferred embodiment, the vector used is pET30a(+) (Novagen, Calif., USA), which contains sequences coding a histidine tag at the N-terminal region for purification.

The vector containing the appropriate DNA sequence as hereinabove described, as well as an appropriate promoter or control sequence, may be employed to transform an appropriate host to permit the host to express the enzyme. "Transformation" includes all forms of causing uptake of foreign DNA by a host cell. The transformed cells are then screened for those which contain the desired DNA and the successful transformants are cultured under conditions which affect the expression of the coding sequences.

Representative examples of appropriate hosts include bacterial cells, such as *E. coli* and *Streptomyces*; fungal cells, such as yeast; insect cells such as *Drosophila* S2 and *Spodoptera* Sf9; animal cells; adenoviruses; plant cells, etc. The selection of an appropriate host is deemed to be within the scope of those skilled in the art from the teachings herein and can include expression host BL21 or BL21 CodonPlus RIL strain (Stratagene).

Following transformation of the host strain, the enzyme is induced by appropriate means (e.g., temperature shift or chemical induction) and cells are cultured for an additional period. One preferred method of induction is through the use of IPTG (Isopropyl-β-D-thiogalactopyranoside). Cells are typically disrupted by physical or chemical means known to those skilled in the art, centrifuged, and the resulting crude extract retained for further purification. Purification of the enzyme or fragment thereof can be carried out by any means known to those skilled in the art and can include chromatographic techniques, such as histidine-tag affinity chromatography and Nickel affinity chromatography. Commercially available kits for this purification can be purchased from vendors (Qiagen, Inc. Chatsworth, Calif.; Novagen, Calif., USA). An immunoassay, such as a Western blot assay, can then be utilized to verify the presence of the recombinant enzyme.

After successful validation against recombinant enzymes, the antibodies developed using the antigenic peptide approach described herein can be used in various immunoassays to detect the induction, expression and regulation of enzymes involved in the ω-oxidation of fatty acids and alkanes in various samples, including fermentation samples, shake flask samples, etc. Use of the subject antibodies is helpful in obtaining a visible picture of the presence and amount of specific enzymes (including degradation) during fermentation. The antibodies may be contacted with the sample for a period of time under assay conditions sufficient for the antibodies to bind to the enzymes, if present. Such time and conditions can be readily determined by persons skilled in the art. After the antibodies have been in contact with the sample for a sufficient period of time to allow the antibodies to bind to the enzymes, such binding may be detected by an immunoassay. Diagnostic assays include methods which utilize the antibody and a label to detect the enzyme. Such assays are well-known to those skilled in the art and include radioimmunoassays, enzyme-linked immunosorbent assays (ELISA), Western blot, immunofluorescent assays, chemiluminescent assays, and bioluminescent assays.

The present invention further provides a method of detecting the presence and amount of a specific enzyme involved in the ω-oxidation of fatty acids and alkanes to α,ω-dicarboxylic acids in a mixture suspected of having such enzyme. The method comprises the steps of generating an antibody which specifically binds to an enzyme lo involved in the ω-oxidation of fatty acids and alkanes to α,ω-dicarboxylic acids, incubating the antibody with the mixture for a time and under conditions sufficient to allow selective binding of the antibody to the specific enzyme and detecting the enzyme-antibody complex. Preferably, the antibody which specifically binds to one particular enzyme involved in the ω-oxidation of fatty acids and alkanes to α,ω-dicarboxylic acids does not also bind to other enzymes involved in the ω-oxidation of fatty acids and alkanes to α,ω-dicarboxylic acids. In one embodiment, in order to detect the presence of the enzyme-antibody complex, a labeled binding partner of the enzyme-antibody complex is added to the mixture to form a labeled complex, and the mixture is analyzed to determine the presence of the labeled complex.

The present invention also provides a method of monitoring the degree of enzyme induction and/or enzyme stability during ω-oxidation of fatty acids or alkanes to dicarboxylic acids. The method comprises the steps of generating an antibody which specifically binds to an enzyme involved in the ω-oxidation of fatty acids and alkanes to α, ω-dicarboxylic acids, incubating the antibody with the mixture for a time and under conditions sufficient to allow selective binding of the antibody to the specific enzyme involved in the ω-oxidation of fatty acids and alkanes to α,ω-dicarboxylic acids, detecting the enzyme-antibody complex, and correlating the amount of enzyme detected with a degree of enzyme induction and/or stability. Preferably, the antibody which selectively binds to one particular enzyme involved in the ω-oxidation of fatty acids and alkanes to α,ω-dicarboxylic acids does not also bind to other enzymes involved in the ω-oxidation of fatty acids and alkanes to α,ω-dicarboxylic acids. In one embodiment, in order to detect the presence of the enzyme-antibody complex, a labeled binding partner of the enzyme-antibody complex is added to the mixture to form a labeled complex, and the mixture is analyzed to determine the presence of the labeled complex.

This method allows the degree of enzyme induction and/or enzyme stability during ω-oxidation of fatty acids and alkanes to dicarboxylic acids to be monitored in a sample by determining whether or not an antibody directed to an enzyme involved in the ω-oxidation of fatty acids and alkanes to α,ω-dicarboxylic acids is bound to such an enzyme. The amount of enzyme and the amount of dicarboxylic acids in the sample can also be monitored to provide information concerning induction of the enzyme in response to substrates and other conditions in fermentation media and their correspondence to efficiency of production of the dicarboxylic acids. The information may then be used to manipulate the amount of enzyme produced by the yeast biocatalyst involved in the ω-oxidation of fatty acids and alkanes to α,ω-dicarboxylic acids and to increase the amount of dicarboxylic acids produced.

The polyclonal or monoclonal antibodies of the present invention may be labeled with a detectable marker after the antibodies have been isolated and purified. Suitable labels may be radioactive or non-radioactive. Common non-radioactive labels include detectable enzymes and fluorescent molecules. Fluorescent molecules absorb light at one wavelength and emit it at another, thus allowing visualization with, e.g., a fluorescent microscope. Spectrophotometers, fluorescence microscopes, fluorescent plate readers and flow sorters are well-known and are often used to detect specific molecules which have been made fluorescent by coupling them covalently to a fluorescent dye. Fluorochromes such as Green Fluorescent Protein (GFP), red shifted mutants of GFP, amino coumarin acetic acid (AMCA), fluorescein isothiocyanate (FITC), tetramethylchodamine isothiocyanate (TRITC), Texas Red, Cy3.0 and Cy5.0 are covalently coupled to antibody molecules in connection with detection using conventional fluorescence microscopy. Radioactive labels may be measured by conventional radiographic techniques.

Cross-linkers suitable for use in coupling a label to an antibody are well-known. Homofunctional and heterobifunctional cross-linkers are all suitable. Reactive groups which can be cross-linked with a cross-linker include primary amines, sulfhydryls, carbonyls, carbohydrates and carboxylic acids.

Cross-linkers are available with varying lengths of spacer arms or bridges. Cross-linkers suitable for reacting with primary amines include homobifunctional cross-linkers such as imidoesters and N-hydroxysuccinimidyl (NHS) esters. Examples of imidoester cross-linkers include dimethyladipimidate, dimethylpimelimidate, and dimethylsuberimidate. Examples of NUS-ester cross-linkers include disuccinimidyl glutamate, disuccinimidyl suberate and bis(sulfosuccinimidyl) suberate. Accessible α amine groups present on the N-termini of peptides react with NHS-esters to form amides. NHS-ester cross-linking reactions can be conducted in phosphate, bicarbonate/carbonate, HEPES and borate buffers. Other buffers can be used if they do not contain primary amines.

Sulfhydryl reactive cross-linkers include maleimides, alkyl halides, aryl halides and α-haloacyls which react with sulfhydryls to form thiol ether bonds and pyridyl disulfides which react with sulfhydryls to produce mixed disulfides. Sulfhydryl groups on peptides and proteins can be generated by techniques known to those with skill in the art, e.g., by reduction of disulfide bonds or addition by reaction with primary amines using 2-iminothiolane. Examples of maleimide cross-linkers include succinimidyl 4-(N-maleimidomethyl) cyclohexane-1-carboxylate and m-maleimidobenzoyl-N-hydroxysuccinimide ester. Examples of haloacetal cross-linkers include N-succinimidyl (4-iodoacetal) aminobenzoate and sulfosuccinimidyl (4-iodoacetal) aminobenzoate. Examples of pyridyl disulfide cross-linkers include 1,4-Di-[3'-2'-pyridyldithio(propionamido)butane] and N-succinimidyl-3-(2-pyridyldithio)-propionate.

Carboxyl groups are cross-linked to primary amines or hydrazides by using carbodimides which result in formation of amide or hydrazone bonds. In this manner, carboxy termini of peptides or proteins can be linked. Examples of carbodiimide cross-linkers include 1-ethyl-3-(3-dimethylaminopropyl)-carbodiimide hydrochloride and N,N'-dicyclohexylcarbodiimide. Arylazide cross-linkers become reactive when exposed to ultraviolet radiation and form aryl nitrene. Examples of arylazide cross-linkers include azidobenzoyl hydrazide and N-5-azido-2 nitrobenzoyloxysuccinimide. Glyoxal cross linkers target the guanidyl portion of arginine. An example of a glyoxal cross-linker is p-azidophenyl glyoxal monohydrate.

Heterobifunctional cross-linkers which possess two or more different reactive groups are suitable for use herein. Examples include cross-linkers which are amine-reactive at one end and sulfhydryl-reactive at the other end such as 4-succinimidyl-oxycarbonyl-α-(2-pyridyldithio)-toluene, N-succinimidyl-3-(2-pyridyldithio)-propionate and the maleimide cross-linkers discussed above.

It is contemplated that signal amplification techniques may be utilized to enhance the sensitivity of assays according to the present invention. Thus, a subject antibody may be detected with a group of secondary labeled ligands which are capable of binding to the antibody. For example, using conventional techniques biotin may be linked to antibodies produced according to the present invention. The biotinylated antibody is then allowed to contact and bind the target enzyme. Streptavidin or avidin which has been labeled with a known label is then contacted with the antibody/enzyme complex which then leads to binding of the labeled streptavidin or avidin to the biotin portion of the biotinylated antibody. Additional biotin may be added followed by the addition of more labeled streptavidin or avidin. Since each streptavidin or avidin molecule is capable of binding four biotin molecules, a relatively large three-dimensional network is created which includes numerous labels which may be detected by conventional fluorescence microscopy or by radiographic techniques. In another embodiment, secondary antibodies may be raised to the antibodies which bind the target enzymes. As described above, the secondary antibodies are marked with a detectable label. In this instance, the primary antibody is bound by a plurality of secondary antibodies incorporating a detectable label. Since a plurality of labels are attracted to the target site, the signal strength is multiplied and more easily detected.

Affinity can be determined through the application of known techniques, providing a measurement of the amount or concentration of the enzymes of the ω-hydroxylase complex in the sample. Affinity may be expressed as an association constant, $K_\alpha$, which is defined as the molar concentration of enzyme-antibody complex divided by the molar concentrations of free antigen and free antibody under equilibrium conditions. The $K_\alpha$ determined for a preparation of polyclonal antibodies, which are heterogeneous in their affinities for multiple enzyme epitopes, represents the average affinity, or avidity, of the antibodies for the enzyme.

Results of the immunoassays can be used to serve as both evidence and a guide in the manipulation of metabolic pathways in an attempt to affect the amount of certain products or by-products of the enzymes. In a preferred embodiment, the target proteins are enzymes involved in the ω-oxidation of fatty acids and alkanes to α,ω-dicarboxylic acids, and the products of interest are ω-dicarboxylic acids.

The following examples are included for purposes of illustration and should not be construed as limiting the present invention.

EXAMPLE 1

Materials and Methods

Antigenic Peptides and Antibody Generation

Peptides were designed from sequence data considering antigenic potential and cross-reactivity. Table 1 sets forth the peptide designation, its amino acid sequence, and its target protein (the protein from which the peptide is derived). Peptides were conjugated lo to a carrier molecule to assist immune system recognition. Antibodies were produced in sheep by The Binding Site Limited, England. The initial target proteins were proteins of CYP52A1, CYP52A2, CYP52A3, CYP52A5, CYP52A8, CYP5D4A, CPR and cytochrom b5. To ensure that at least one set of specific antibodies was produced, two peptides (one from the C-terminus and one from the N-terminus) were selected for antibody generation and at least two animals were used for every antigenic peptide. IgG fractions were purified from the antisera and further tested as described in Example 3.

Protein Induction

20–50 ml LB kan medium were inoculated in a 250-mL flask with a fresh overnight culture. The culture was incubated at 37° C. shaker until $O.D._{600}$~0.4–0.6. An aliquot (1 mL sample) was taken (time 0) and IPTG stock solution (0.1 M) was added to the flask to a final concentration of 1 mM. The culture was induced for 5 hours. 1 mL samples were taken every hour. Cells were spun down from all samples and stored at −20° C. freezer until ready to analyze. 100 μL 2×SDS sample buffer was added to each sample and vortexed to mix thoroughly. Samples were then boiled in water for 5 minutes and cooled to room temperature. 15 μL of each sample was loaded into precast SDS-PAGE gels. A prestained protein molecular weight marker mix (such as the BlueRanger marker mix from Pierce Biotechnology, Inc., Rockford, Ill.) was also loaded. Gels were run at 20 mA constant current until the blue dye reached the bottom of the gels. Gels were stained with GelCode Blue (Pierce) according to manufacture's protocol. Proteins of interest were located using the molecular weight markers and induction intensities compared over time. Optimal induction times for protein induction and purification were selected.

Recombinant Protein Purification (Under Denatured Conditions)

100 ml LB kan medium was inoculated in a 500 mL flask with a fresh overnight culture. Cultures were incubated at 37° C. shaker until O.D.600 ~0.4–0.6. IPTG stock solution was added to flasks to a final concentration of 1 mM. The cells were harvested when induction reached the optimal

TABLE 1

Antigenic peptides designed for recombinant antibody generation

| Peptide | Peptide sequence | | Target Protein |
|---|---|---|---|
| A1-426-442 | YAAHRNPAVYGKDALEF | (SEQ ID NO:15) | CYP52A2A |
| A1-61-83 | ELLKKKSDGTLIDFTLQRIHDLD | (SEQ ID NO:16) | CYP52A2A |
| B1-445-460 | ATHRDPSIYGADADVF | (SEQ ID NO:17) | CYP52A3A |
| B1-92-109 | GLWNNKYIVRDPKYKTTG | (SEQ ID NO:18) | CYP52A3A |
| C1-411-435 | QKGEAVSYGINSTHLDPVYYGPDAA | (SEQ ID NO:19) | CYP52A5A |
| C1-59-81 | QFKKEGRAQEYNDYKFDHSKNPS | (SEQ ID NO:20) | CYP52A5A |
| D1-213-231 | YDEKLCIPTPNEIPGRENF | (SEQ ID NO:21) | CYP52A1A |
| D1-424-438 | AYVVYKTHRLEEYYG | (SEQ ID NO:22) | CYP52A1A |
| D1-490-504 | QMFETVSSDPGLEYP | (SEQ ID NO:23) | CYP52A1A |
| D1-75-91 | ANFADEVFDEYPNHTFY | (SEQ ID NO:24) | CYP52A1A |
| E1-205-221 | EEIGYDTKDMSEERRRF | (SEQ ID NO:25) | CYP52A8A |
| E1-40-63 | FTHVQRDGWLGFKFGREFLKAKSA | (SEQ ID NO:26) | CYP52A8A |
| E1-406-427 | RKDEVVQYSISATQTNPAYYGA | (SEQ ID NO:27) | CYP52A8A |
| E1-73-95 | RFHDNEDTFSSYAFGNHVVFTRD | (SEQ ID NO:28) | CYP52A8A |
| F1-490-499 | LNGVYIRTRTLNGVYIRTRT | (SEQ ID NO:29) | CYP52D4A |
| F1-72-91 | SVKRFESAPHPQNKTLVNRA | (SEQ ID NO:30) | CYP52D4A |
| Y1-180-201 | EYAEGDDGTGTLDEDFMAWKDN | (SEQ ID NO:31) | NCP1A |
| Y1-657-679 | SEDKAAELVKSWKVQNRYQEDVW | (SEQ ID NO:32) | NCP1A | time determined by the induction experiment. Cells were lysed and His-tagged recombinant proteins were purified using Ni-NTA spin column (Qiagen) according to manufacture's protocol. Samples were taken from every step of the purification and analyzed on SDS-PAGE to determine the efficiency of the purification.

SDS-PAGE

Precast SDS-PAGE gels (Bio-Rad) were assembled into a Protean II unit (Bio-Rad). SDS-PAGE running buffer (Bio-Rad) was placed into the upper and lower reservoir to fill. Protein samples, markers and controls were loaded into the wells. Gels were run at 10 mA for 5 min and then the current increased to 20 mA. The power was turned off when the blue dye reached the bottom of the gels. The unit was disassembled according to manufacture's instructions (Bio-Rad).

Protein Transfer (Bio-Rad Trans-Blot Semi-Dry Unit)

Each SDS-PAGE gel was placed in transfer buffer (for 1L: 5.82 g Tris, 2.93 g glycine, 3.25 mL 10% SDS, 200 mL MeOH) for 10 minutes. A piece of nitrocellulose membrane was cut to the size of the gel and the direction of the membrane labeled. The membrane was wet in the transfer buffer. Two pieces of thick filter paper (Blot paper, Bio-Rad) were cut to the size of the gel. The filter paper was saturated by soaking in the transfer buffer. The safety cover and the stainless steel cathode assembly from the transfer unit was removed. A pre-soaked sheet of filter paper was placed onto the platinum anode. A pipet was rolled over the surface to exclude all air bubbles. The pre-wetted membrane was placed on top of the filter paper and air bubbles rolled out. The equilibrated gel was placed on top of the membrane and again, all air bubbles were rolled out. Another sheet of pre-soaked filter paper was placed on top of the gel and all air bubbles were rolled out. The cathode was placed carefully onto the stack. The latches with guide posts were engaged by pressing without disturbing the filter paper stack. The safety cover was placed on the unit and the unit plugged into the power supply. The power supply was turned on and mini gels were transferred for 30 min at 10–15 V (current limit at 5 mA/cm$^2$). After transfer, the power supply was turned off and the unit disassembled. Gels were washed in water for 2×5 minutes and stained with GelCode Blue to check for transfer efficiency. The membrane was removed and used for Western blot.

Western Blot

Membranes were equilibrated in TBST for 5 minutes followed by incubation in a blocking solution (SuperBlock, Pierce) for 1 hour. Membranes were incubated for 4 hours with the primary antibody diluted in the blocking solution. Membranes were washed three times with 5 min washes in TBST. Membranes were incubated for 1 hr with HRP conjugated Monkey-anti-Sheep antibody diluted in TBST, followed by three washes of 5 minutes each in TBST. Membranes were then washed in TBS for 5 minutes followed by placement in an opened plastic page protector. Chemiluminescent substrate (SuperSignal, Pierce), was added and the membranes incubated for 1 min at room temperature. Excessive substrate was removed and the membranes covered between the page protector sheets. Membranes were placed inside a film cassette, a chemiluminescent film was placed over the membranes and the cassette closed. The chemiluminescent film was exposed for 2–4 hours. The film was then developed, washed in water and air dried.

Fermentation Sample Preparation

Samples were taken from fermentor or mini-fermentor and washed in ice cold 50 mM HEPES buffer (pH 7.6) repeatedly until the samples were freed of diacid. Cells were resuspended in a phosphate buffer (100 mM phosphate buffer pH 7.6, 20% glycerol, and 1 mM PMSF). Cells were broken open in a bead beater (for samples from mini-fermentor) or put through a French Press (for samples from 10 L fermentor). Cell debris was spun down at 16,000 g for 30 minutes and supernatants transferred to a new tube. Samples were kept on ice or in the freezer for further analysis.

EXAMPLE 2

Recombinant Protein Expression and Purification

The coding regions of the DNA sequences of the enzymes from which the antigenic peptides were synthesized (see Table 1) were cloned into pET30a(+) (Novagen, Calif., USA) using high fidelity PCR according to the manufacturer's protocol using the templates and primers shown in Table 2. The sequences of these expression vectors were verified by DNA sequencing. The pET30 (+) vector vectors contain sequences coding for a histidine tag at the N-terminal region that can be used to purify the attached enzyme. Host strains BL21 or BL21 CodonPlus RIL (commercially available from Novagen) were transformed to produce the subject enzymes. Table 3 lists the recombinant protein expression strains, describes the vectors contained therein and the antibiotic resistance genes carried by the vectors. Strains are based on BL21 strains and designated HCC001 through HC005 depending on the ORF of the introduced genetic construct.

Single colonies of host strain carrying the expression vector were selected and used to inoculate tubes containing 3 ml LB medium with antibiotics. The culture was allowed to grow overnight in a 37° C. shaker. Flasks were inoculated with 10 ml LB medium containing antibiotics to $OD_{600}$ of 0.1 and then the overnight culture was introduced into the flasks and allowed to grow at 37° C. until $OD_{600}$ was 0.6.

One ml samples were taken as noninduced control (t=0) and stored at −20° C. Expression was induced by adding IPTG (Isopropyl-β-D-thiogalactopyranoside) to obtain a final concentration of 1 mM and the cultures were then grown for an additional 5 hours. One ml samples were taken at hourly intervals and stored at −20° C. The samples were centrifuged to collect cells, which were then mixed with 100 μl of SDS-PAGE sample buffer and boiled for 5 minutes. 10 μl of the samples were then loaded on SDS-PAGE gel and run at constant current of 20 mA. After running the gel, enzymes on the gel were visualized by staining with GelCode Blue stain reagent (Pierce, Rockford, Ill.). The strain and time of induction were determined by the induction profile on the gel.

The induction process was repeated for the best strain with optimal induction time (Table 4) and those cells were collected for purification by histidine-tag affinity chromatography. The expressed histidine-tagged enzymes were found in inclusion bodies and therefore insoluble. Enzyme purification was conducted under denaturing conditions using 8M of Urea to solubilize the enzyme in inclusion bodies. Nickel affinity columns were used to purify the enzymes.

The sequences of these constructed expression vectors were verified by DNA sequencing. The strains were grown at 37° C. until $OD_{600}$ at 0.4 to 0.6 and induced with 1 mM IPTG. Samples were taken after IPTG at one-hour intervals and were analyzed on SDS-PAGE to determine the best induction time. Recombinant proteins were produced by the same approach using the best induction time (FIG. 1). His-tagged proteins were purified under denatured conditions according to manufacture's protocol.

TABLE 2

Templates and Primers for PCR Amplification of Selected *C.tropicalis* Genes

| Gene | Template | Primers | Primer Sequences (5'→3') | | Sites |
|------|----------|---------|--------------------------|---|-------|
| CYP52A1A | pHKM11 | 3742-99A | TATACCAACCAACCATGGCCACACAAGAAATC | (SEQ ID NO:1) | NcoI |
| | | 3742-99B | GCAGCTCTCGAGTTACATCTTGACAAAGACACC | (SEQ ID NO:2) | XhoI |
| CYP52A2A | pPA15 | 3742-18A | CACGACCATGGCTGTACACGATATTATCGCCAC | (SEQ ID NO:3) | NcoI |
| | | 3742-18B | CACGCTCGAGCTAATACATCTCAATATTGGC | (SEQ ID NO:4) | XhoI |
| CYP52A5A | pPAL3 | 3742-18C | GCACACCATGGTTGAACAACTCCTAGAATATTGG | (SEQ ID NO:5) | NcoI |
| | | 3742-18D | CGGACTCGAGCTAGTCAAACTTGACAATAGCACC | (SEQ ID NO:6) | XhoI |
| CYP52A8A | pHKM12 | 3742-18E | CGCTACCATGGTCGATCAGATCTTACATTACTGG | (SEQ ID NO:7) | NcoI |
| | | 3742-18F | CGTTCTCGAGCTATGACATCTTGACGTGTGC | (SEQ ID NO:8) | XhoI |
| CYP52D4A | pHKM13 | 3950-6C | AAGGCCATGGCTATATCTAGTTTGCTATCG | (SEQ ID NO:9) | NcoI |
| | | 3950-6D | CGGAATTCTCAAGTTCTAGTTCGGATGTA | (SEQ ID NO:10) | EcoRI |
| CPRA | pHCC001 | 3742-18G | CGACGGATCCATGGCTTTAGACAAGTTAGATTTG | (SEQ ID NO:11) | BamHI |
| | | 3742-18H | CCGGAAGCTTCTACCAAACATCTTCTTGGTATC | (SEQ ID NO:12) | HindIII |
| Cytochrome b5 | pHKM17 | 3950-6A | AAGGCCATGGCCGACACAGACACCACGACC | (SEQ ID NO:13) | NcoI |
| | | 3950-6B | GTGCTCGAGTTAGGCAAAGTTGGTCTTGTA | (SEQ ID NO:14) | XhoI |

TABLE 3

Recombinant protein expression strains

| Strain | Description | Antibiotics |
|--------|-------------|-------------|
| NovaBlue | Novagen non-expression host for cloning and plasmid preps | Tetracycline |
| BL21(DE3) | Novagen general purpose expression host | None |
| BL21(DE3)pLysS | Novagen high-stringency expression host | Chloramphenicol |
| Novagen Control G | β-galactosidase expressing strain | Kanamycin |
| BL21 CodonPlus RIL | Stratagene codon bias-adjusted protein expression host | None |
| HCC001 | CYP52A2A expressing strain containing pET/A2A vector | Kanamycin |
| HCC002 | CYP52A5A expressing strain containing pET/A5A vector | Kanamycin |
| HCC003 | Reductase expressing strain containing pET/NCP1 vector | Kanamycin |
| HCC004 | CYP52A8A expressing strain containing pET/A8A vector | Kanamycin |
| HCC005 | CYP52A1A expressing strain containing pET/A1A vector | Kanamycin |
| HCPR | Reductase expressing vector pET/NCP1 in BL21 CodonPlus strain | Kanamycin |
| Hb5 | Cytochrome b5 expression strain containing pET/b5 vector | Kanamycin |

TABLE 4

Optimal IPGT induction time for His-tagged recombinant protein expression

| Strain | Construct | Protein | Induction Time |
|---|---|---|---|
| HCC001 | pET/A2 | CYP52A2A | 3 hours |
| HCC002 | pET/A5 | CYP52A5A | 3 hours |
| HCC003 | pET/NCP1 | Reductase | 2 hours |
| HCC004 | pET/A8 | CYP52A8A | 3 hours |
| HCC005 | pET/A1 | CYP52A1A | 3 hours |
| Hb5 | pET/b5 | cytochrome b5 | 1 hours |

EXAMPLE 3

Screening of Polyclonal Antibodies

Antisera from sheep injected with the antigenic peptides of Example 1 were collected and evaluated for titer. Sheep producing weak responses were reboosted. IgG fractions from antisera showing adequate responses were further evaluated and tested for strength and specificity of response to the array of antigenic peptides. Antibodies demonstrating good strength and specificity were subject to further screening and validation using the recombinant histidine-tagged enzymes described in Example 2. Antibodies were screened against the recombinant enzymes for their reactivity and specificity using dot-blots and Western blots. The following Western blot protocol was developed to determine antibody specificity to the various enzymes. The nitrocellulose membrane was rinsed briefly with TBST (20 mM Tris, 500 mM NaCl, 1% Tween 20, pH 7.5) and incubated in the blocking solution for 1 hour. The primary solution was diluted with blocking solution (BlockerJ BSA in TBS, Pierce, Rockford, Ill.) and the membrane was then incubated with the antibody solution for 4 hours. The membrane was washed five times in TBST, with each wash taking 15 minutes. The membrane was then incubated with enzyme-conjugated secondary antibody (donkey anti-goat/sheep immunoglobulin-peroxidase, The Binding Site, Birmingham, UK) for 1 hour. The membrane was washed five times in TBST (15 minutes for each wash) and rinsed briefly in TBS (20 mM Tris, 500 mM NaCl, pH 7.5). The membrane was then incubated in substrate solution (SuperSignal West Pico Chemiluminescent Substrate, Pierce, Rockford, Ill.) for 1 minute, excessive solution was drained, and the membrane was exposed to a chemiluminescent film (Hyperfilm ECL, Amersham Life Science, Beckinghamshire, England) which was then developed. Various dilution rates were tested to determine the best conditions for specificity and minimize cross-reactivity.

Antibody Screening

IgG fractionated antibodies were screened against their antigenic peptides and corresponding protein. A good antibody would react strongly to the antigenic peptides and the whole protein and little or no background reaction to other peptides and proteins.

Antibodies were first screened against antigenic peptides using dot blots. Antigenic peptides were individually diluted in 1% SDS to 0.3 μg/μl and boiled for 5 min to complete denaturation and solubilization. Dampened nitrocellulose membranes were spotted with 1.0 μl of each peptide in a grid pattern and then dried. Each blocked membrane was incubated with one of the P450 or reductase primary antibody. Membranes were washed and then incubated in a HRP conjugated donkey-anti-sheep/goat secondary antibody. The peptide-antibody binding was detected with the SuperSignal chemiluminescent substrate (Pierce).

TABLE 5

Antibody Screen against Antigenic Peptides

| Antibody | From Peptide | A1-61-83 | A1-426-442 | B1-92-109 | B1-445-460 | C1-59-81 | C1-411-435 | D1-75-91 | D1-213-231 | E1-73-95 | E1-205-221 | E1-406-427 | F1-72-91 | F1-490-499 | Y1-180-201 | Y1-657-679 |
|---|---|---|---|---|---|---|---|---|---|---|---|---|---|---|---|---|
| CUS1393.A1.3 | A1-61-83 | 5 | 0 | 0 | 0 | 2 | 1 | 0 | 0 | 0 | 0 | 0 | 0 | 0 | 2 | 1 |
| CUS1393.B1.2 | A1-426-442 | 0 | 5 | 0 | 1 | 0 | 0 | 0 | 0 | 0 | 0 | 0 | 0 | 0 | 0 | 0 |
| CUS1393.B1.3 | A1-426-442 | 0 | 5 | 0 | 0 | 0 | 0 | 0 | 0 | 0 | 0 | 0 | 0 | 0 | 0 | 0 |
| CUS1393.B2.2 | A1-426-442 | 0 | 2 | 0 | 1 | 0 | 0 | 0 | 0 | 0 | 0 | 0 | 0 | 0 | 0 | 0 |
| CUS1394.A1.2 | B1-92-109 | 1 | 0 | 1 | 5 | 2 | 0 | 0 | 0 | 0 | 0 | 0 | 0 | 0 | 1 | 2.5 |
| CUS1394.A2.2 | B1-92-109 | 0 | 0 | 5 | 0 | 0 | 0 | 0 | 2.5 | 0 | 0 | 0 | 0 | 0 | 0.5 | 0.5 |
| CUS1934.A2.3 | B1-92-109 | 0 | 0 | 0 | 0 | 0 | 0 | 0 | 0 | 0 | 0 | 0 | 0 | 0 | 0 | 0 |
| CUS1394.B1.2 | B1-445-460 | 0 | 0 | 0 | 3 | 0 | 0 | 0 | 0 | 0 | 0 | 0 | 0 | 0 | 0 | 0 |
| CUS1394.B1.3 | B1-445-460 | 0 | 0 | 0 | 5 | 0 | 0 | 0 | 0 | 0 | 0 | 0 | 0 | 0 | 0 | 0 |
| CUS1394.B2.2 | B1-445-460 | 0.5 | 1 | 0 | 5 | 2 | 0 | 0 | 0 | 0 | 0 | 0 | 0 | 0 | 0 | 0 |
| CUS1395.A1.3 | C1-59-81 | 0 | 0 | 0 | 0 | 3.5 | 0 | 0 | 0 | 0 | 0 | 0 | 0 | 0 | 0 | 0 |
| CUS1395.B2.2 | C1-411-435 | 0 | 0 | 0 | 0 | 0 | 3 | 0 | 0 | 0 | 0 | 0 | 0 | 0 | 0 | 0 |
| CUS1395.B2.3 | C1-411-435 | 0 | 0 | 0 | 0 | 0 | 5 | 0 | 0 | 0 | 0 | 0 | 0 | 0 | 0 | 0 |
| CUS1396.A1.2 | Y1-657-679 | 1 | 0 | 1 | 2 | 2 | 0 | 0 | 0 | 0 | 0 | 0 | 0 | 0 | 1 | 4 |
| CUS1396.A2.2 | Y1-657-679 | 0 | 0 | 0 | 0 | 0 | 0 | 0 | 0 | 0 | 0 | 0 | 0 | 0 | 0.5 | 2.5 |
| CUS1396.A2.3 | Y1-657-679 | 0 | 0 | 0 | 0 | 0 | 0 | 0 | 0 | 0 | 0 | 0 | 0 | 0 | 0 | 5 |
| CUS1396.B1.2 | Y1-180-201 | 0 | 0 | 0 | 2 | 0 | 0 | 0 | 0 | 0 | 0 | 0 | 0 | 0 | 5 | 0 |
| CUS1396.B2.2 | Y1-180-201 | 0.5 | 0.5 | 0 | 0 | 0 | 0.5 | 0.5 | 0 | 0 | 0.5 | 0 | 0 | 0 | 5 | 0 |
| CUS1444.A1.1 | D1-213-231 | 1 | 0 | 0 | 0 | 0 | 0 | 0 | 2 | 0 | 0 | 0 | 0 | 0 | 0 | 0 |
| CUS1444.B1.1 | D1-213-231 | 0.5 | 0 | 0 | 0 | 0 | 0 | 0 | 0 | 0 | 0 | 0 | 0 | 0 | 0 | 0 |
| CUS1444.B2.1 | D1-75-91 | 0 | 0 | 0 | 0 | 0 | 0 | 1 | 0 | 0 | 0 | 0 | 0 | 0 | 0 | 0 |
| CUS1445.A1.1 | E1-73-95 | 0 | 0 | 0 | 0 | 0 | 0 | 0 | 0 | 0 | 0 | 0 | 0 | 0 | 0 | 0 |
| CUS1445.B1.1 | E1-205-221 | 0 | 0 | 0 | 0 | 0 | 0 | 0 | 0 | 0 | 0 | 0 | 0 | 0 | 0 | 0 |

TABLE 5-continued

Antibody Screen against Antigenic Peptides

| Antibody | From Peptide | A1-61-83 | A1-426-442 | B1-92-109 | B1-445-460 | C1-59-81 | C1-411-435 | D1-75-91 | D1-213-231 | E1-73-95 | E1-205-221 | E1-406-427 | F1-72-91 | F1-490-499 | Y1-180-201 | Y1-657-679 |
|---|---|---|---|---|---|---|---|---|---|---|---|---|---|---|---|---|
| CUS1445.B1.3 | E1-205-221 | 0 | 0 | 0 | 0 | 0 | 0 | 0 | 0 | 0 | 0 | 0 | 0 | 0 | 0 | 0 |
| CUS1478.B2.1 | F1-490-499 | 0 | 0 | 0 | 0 | 0 | 0 | 0 | 0 | 0 | 0 | 0 | 0 | 0 | 0 | 0 |

Figure 2A:
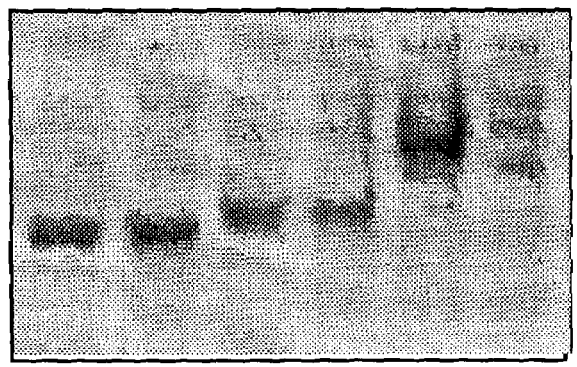
FIG. 2A shows a Commassie stained SDS-PAGE gel showing recombinant proteins expressed in *E. coli*.
Figure 2B:
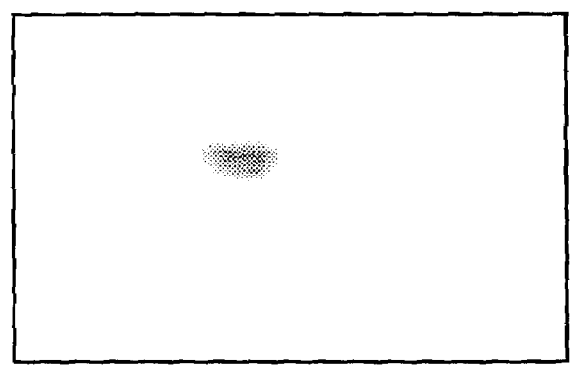
FIG. 2B shows a Western blot indicating the detection of CYP52A5 proteins after transferring the sample set of proteins onto nitrocellulose membrane and reacted with CYP52A5 specific antibody (CUS1395.A1.3).

Scoring: 5 = strong reaction; 3 = intensity of positive control, Sheep IgG; 0.5 = barely visible reaction; 0 = no response detected Most antibodies were active and specific toward the corresponding antigenic peptides. However, a few antibodies failed to recognize any of the antigenic peptides. Antibodies that showed strong and specific reaction to the antigenic peptides were analyzed further against recombinant His-tagged proteins in Western blots. Proteins were separated on SDS-PAGE gels and transferred onto nitrocellulose membranes. The membranes were incubated with primary antibody, secondary antibody, and the antibody-protein interaction was detected using chemiluminescent substrate. FIGS. 2A and 2B illustrate how antibodies were tested for specificity. FIG. 2A shows a Commassie stained SDS-PAGE gel run with recombinant proteins expressed in E. coli. FIG. 2B shows a Western blot of the same gel reacted with a CYP52A5 antibody.

One antibody was chosen for every targeted protein after screening with dot blot and Western blot. The antibody was further tested against serial dilutions of the targeted protein. The antibody sensitivity was measured as the minimal amount of targeted protein needed to be detected by the antibody using the optimal Western blot protocol.

Detection Limit

Figure 3:
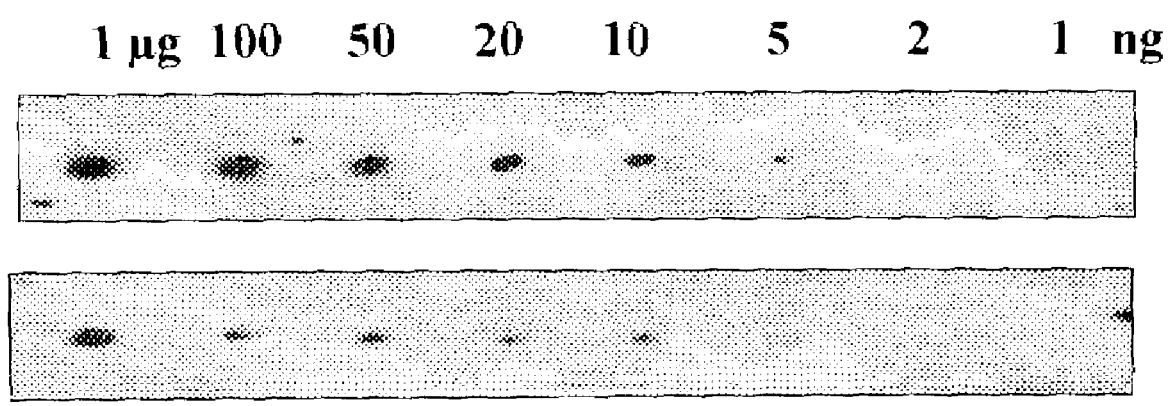
FIG. 3 shows a dot-blot showing the detection limit for CYP52A5 (top) and CYP52A2 (bottom) after incubating the corresponding antibodies with a serial dilution of purified targeted proteins.

The detection limit was obtained by doing dot blots with a serial dilution of known amount purified protein. The detection limit is the smallest amount of targeted protein needed to generate a positive signal in the defined condition and procedure. FIG. 3 shows examples of the detection limit on dot blots.

Table 6 lists the antibody dilution ratio and the detection limit for CYP52A1, CYP52A2, CYP52A5, CYP52A8, and the reductase protein.

TABLE 6

Detection limit of antibodies selected for Western blot

| Target Protein | Antibody Name | Dilution | Detection Limit |
|---|---|---|---|
| CYP52A1A | CUS1444.A1.1 | 1:10,000 | 10 ng |
| CYP52A2A | CUS1393.B1.2 | 1:5,000 | 2 ng |
| CYP52A5A | CUS1395.A1.3 | 1:20,000 | 1 ng |
| CYP52A8A | CUS1445.C2.1 | 1:10,000 | 2–5 ng |
| Reductase | CUS1396.A2.2 | 1:10,000 | 2 ng |

Strain Evaluation Using Recombinant Antibodies

Genetically modified C. tropicalis strains were tested in the mini-fermentor system as well as regular 10 L fermentors. Samples were taken during the course of the fermentation. Samples were run on SDS-PAGE gels and analyzed by Western blot.

Strains were analyzed for the targeted protein corresponding to the genetic modifications. Many strains were evaluated by more than one antibody. These strains can be categorized into three groups: the base stains/control strains upon which the genetic manipulation was based; strains with additional copies of gene(s); and strains with promoter-gene fusion(s). For individual strains, the Western analysis identifies the induction of the targeted protein over time and its stability. For strain comparison, the modified strain was always compared to its base strain to evaluate the effects of the genetic modification on the expression of the corresponding protein. (FIG. 5). The results from the 10 L fermentation runs are directly comparable.

Expression Over Time

Table 7 shows the expression of various proteins during the conversion phase of the fermentation. Samples were taken before and after a fatty acid substrate was added. Samples were washed as described and cells were broken by French Press. The same volume of samples was loaded to give a correlation between protein expression and productivity on the volume bases.

TABLE 7

Western blot analysis: Protein induction during fermentation

| | Induction Time (hr) | | | | | | |
|---|---|---|---|---|---|---|---|
| | 0 | 5 | 23 | 48 | 71 | 96 | 120 |
| CYP52A1 Protein | − | − | − | − | − | − | − |
| CYP52A2 Protein | − | +++ | ++ | + | − | − | − |
| CYP52A5 Protein | − | +++ | ++ | ++ | + | + | + |
| Reductase Protein | − | ++ | ++ | ++ | ++ | ++ | + |

Ferementation strain: HDC 23-3
Sample Loaded: 10 μL
Run Number: 3538-239
SDS-PAGE Gel: 10%

The strain HDC23-3 has additional copies of CYP52A2 and NCP1 gene. The results clearly showed that CYP52A2, CYP52A5, and reductase proteins were induced by the substrate. CYP52A2 protein was induced in the first 48 hours and subsequently disappeared. CYP52A5 protein was induced throughout the fermentation with the strongest induction early in the fermentation. The reduction protein was induced throughout the fermentation and almost maintained the same induction level.

When samples were adjusted for their protein concentration, the induction showed the same proteins were induced and the induction pattern were very similar. (Table 8).

TABLE 8

Western blot analysis: Protein induction during fermentation

| | Induction Time (hr) | | | | | | |
|---|---|---|---|---|---|---|---|
| | 0 | 4 | 8 | 20 | 45 | 69 | 95 | 119 |
| CYP52A1 Protein | − | − | − | − | − | − | − | − |
| CYP52A2 Protein | − | +++ | ++ | − | − | − | − | − |

TABLE 8-continued

Western blot analysis: Protein induction during fermentation

| | Induction Time (hr) | | | | | | |
|---|---|---|---|---|---|---|---|
| | 0 | 4 | 8 | 20 | 45 | 69 | 95 | 119 |
| CYP52A5 Protein | – | +++ | ++ | + | – | – | – | – |
| Reductase Protein | – | ++ | + | + | +++ | +++ | +++ | ++ |

Ferementation strain: HDC 23-3
Sample Loaded: ~15 µg
Run Number: 3538-249
SDS-PAGE Gel: 10%

Due to the fluctuation of protein content among the fermentation samples, the ~15 µg samples loaded onto the SDS-PAGE gel represents 3–12 µL of samples. Comparing the two tables, the analysis with protein content adjusted to 15 µg had less amount of proteins loaded onto the SDS-PAGE gel and hence resulted in lower sensitivity in detecting expression in some samples, such as the expression of CYP52A5 protein in the late time points.

Strain Comparison

Western blot analysis can also be used to evaluate different strains. The following table showed the reductase protein induction in three strains: H5343 (the base strain), HDC23-3 (the strain with additional copies of native reductase genes), and PR12 (the strain with additional copies of ppox4NCP1 promoter-reductase fusion). Samples were taken from the same mini-fermentor run and 20 µL of samples were loaded onto 10% precasted SDS-PAGE gels. The reductase antibody was used in the Western blot analysis. Results clearly show that insertion of a strong promoter in front of the reductase gene (strain PR12) significantly increased the level and duration of reductase protein induction, with the promoter fusion strain exhibiting the highest level of reductase (Table 9). These results were further confirmed by the enzymatic reductase assay.

TABLE 9

Western blot analysis: Reductase induction during fermentation

| | Induction Time (hr) | | | | | |
|---|---|---|---|---|---|---|
| | 0 | 4 | 19 | 28 | 42 | 70 |
| H5343 | – | + | ++ | + | + | – |
| HDC23-3 | – | + | ++ | ++ | ++ | + |
| PR12 | – | +++ | +++ | +++ | +++ | ++ |

EXAMPLE 4

Detecting Enzymes in Fermentation Samples

Alkanes and fatty acids were added to a flask in the presence of the yeast C. tropicalis using the fatty acid feed stream (commercial oleic acid) as described in U.S. Pat. No. 6,331,420, and the ω-oxidation of fatty acids to alpha, ω-dicarboxylic acids was allowed to proceed. Fermentation samples were taken at various time intervals such as 0, 4, 8, 20, 27, 44, 70, and 104 hours. Cells were collected by centrifugation and washed three times in ice cold 50 mM HEPES buffer (pH 7.6). The cells were then resuspended in phosphate buffer (100 mM phosphate buffer pH 7.6, 20% glycerol, 1 mM PMSF) and disrupted by passing them through a pre-chilled French Press cell (three times) at 26,000 psi. The cells were centrifuged again at 16,000 rpm for 30 minutes, and the supernatant was collected. The protein concentration from the supernatant was determined using the Bradford protein assay.

A Western blot protocol was developed to detect the presence of the various enzymes. The fermentation sample was subjected to SDS polyacrylamide-gel electrophoresis (SDS-Page) in accordance with the following steps. The fermentation sample was mixed with SDS-PAGE sample buffer in a 1:1 ratio (2×). The mixture was boiled for 5 minutes and allowed to cool to room temperature. The enzyme samples were then loaded onto an SDS-PAGE gel and run at 20 mA constant current. The SDS-PAGE gel was briefly washed in distilled water. The gel was equilibrated in protein transfer buffer (48 mM Tris, 39 mM glycine, 0.037% SDS, 20% methanol). A piece of nitrocellulose membrane was cut to the size of the gel and wetted with transfer buffer. Two pieces of blotting paper (Bio-Rad, Hercules, Calif.) were then cut to the size of the gel and wetted with the transfer buffer. A transfer sandwich was assembled in the order of: blotting paper-nitrocellulose membrane-SDS-PAGE gel-blotting paper. The enzymes from the SDS-PAGE gel were transferred to the nitrocellulose membrane using a semi-dry protein transfer unit (Bio-Rad, Hercules, Calif.) according to the manufacturer's directions. The membrane was then rinsed with water.

Figure 4A:
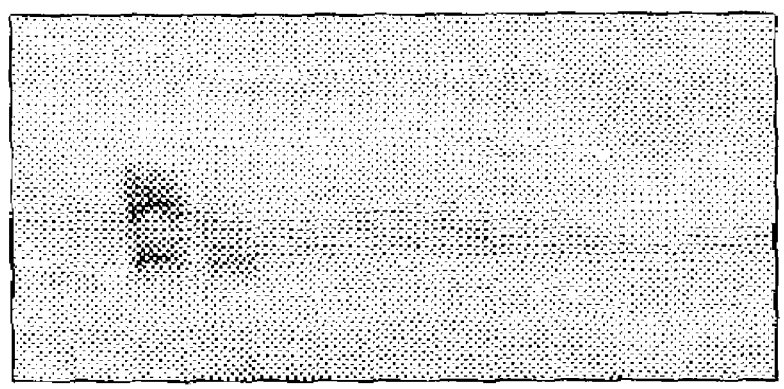
FIG. 4A is a gel showing induction of CYP52A2 during conversion of high oleic fatty acids. Samples were taken from a 10L fermentation run of strain HDC23-3.
Figure 4B:
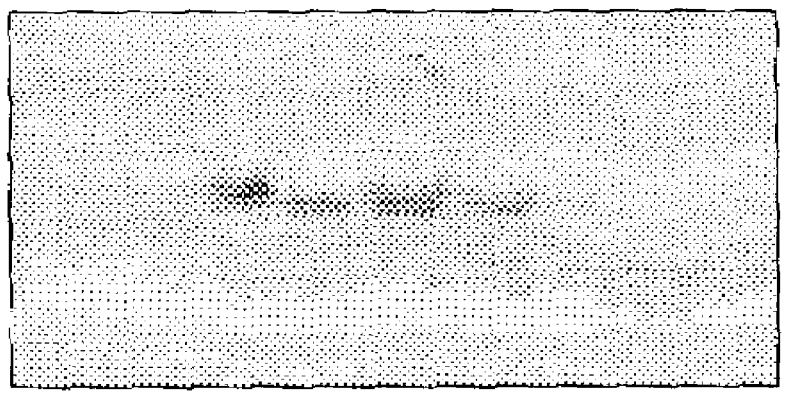
FIG. 4B is a gel showing induction of CYP52A5 during conversion of high oleic fatty acids. Samples were as described in FIG. 4A.
Figure 4C:
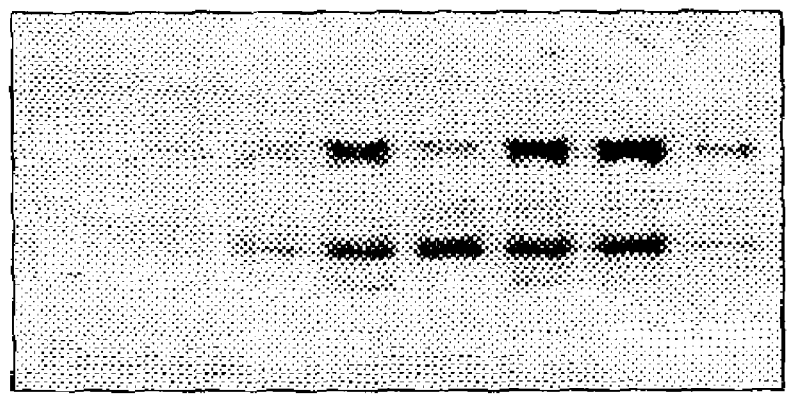
FIG. 4C is a gel showing induction of reductase during conversion of high oleic fatty acids. Samples were as described in FIG. 4A.

The membrane was then washed with water and TBST, incubated in blocking solution for 1 hour, and then incubated in primary antibody for 4 hours. The membrane was then washed five times in TBST (10 minutes for each washing). The membrane was incubated in secondary antibody for 1 hour, after which it was again washed five times in TBST (10 minutes for each washing). The membrane was then briefly rinsed in TBS (20 mM Tris, 500 mM NaCl, pH 7.5) and incubated in substrate solution (SuperSignal West Pico Chemiluminescent Substrate, Pierce, Rockford, Ill.) for 1 minute. The excess solution was drained and the membrane was exposed to a chemiluminescent film (Hyperfilm ECL, Amersham Life Science, Beckinghamshire, England), which was then developed. FIGS. 4A through 4C show induction of CYP52A2, CYP52A5, and reductase in samples taken at time intervals 0, 4, 8, 20, 27, 44, 70, and 104 hours, and illustrate the usefulness of the subject antigenic antibodies produced using the subject antigenic peptides in monitoring enzyme induction and/or enzyme stability during oxidation of fatty acids or alkanes to dicarboxylic acids.

What is claimed is:

1. A method of detecting the presence and amount of a specific enzyme involved in the ω-oxidation of fatty acids and alkanes to α,ω-dicarboxylic acids in a mixture suspected of having said enzyme wherein the specific enzyme comprises the amino acid sequence of SEQ ID NO: 15 and SEQ ID NO: 16, the method comprising:

generating an antibody which specifically binds to the antigenic peptide of SEQ ID NO:15 or the antigenic peptide of about SEQ ID NO:16, incubating the antibody with the mixture for a time and under conditions sufficient to allow binding of the antibody to the specific ω-hydroxylase enzyme, detecting the enzyme-antibody complex, and determining the amount of the enzyme-antibody complex.

2. The method of claim 1 wherein the enzyme involved in the ω-oxidation of fatty acids and alkanes to α,ω-dicarboxylic acids is cytochrome P450 monooxygenase.

* * * * *